US010433907B2

(12) United States Patent
Kelly et al.

(10) Patent No.: US 10,433,907 B2
(45) Date of Patent: Oct. 8, 2019

(54) LOW PROFILE CATHETER ASSEMBLIES AND ASSOCIATED SYSTEMS AND METHODS

(71) Applicant: Medtronic Ardian Luxembourg S.a.r.l., Luxembourg (LU)

(72) Inventors: Tomas Kelly, Ballybrit (IE); Simon Kiersey, Ballybrit (IE)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 449 days.

(21) Appl. No.: 15/405,353

(22) Filed: Jan. 13, 2017

(65) Prior Publication Data

US 2017/0128129 A1 May 11, 2017

Related U.S. Application Data

(62) Division of application No. 14/208,769, filed on Mar. 13, 2014, now Pat. No. 9,579,149.

(51) Int. Cl.
*A61B 18/14* (2006.01)
*A61N 7/02* (2006.01)
(Continued)

(52) U.S. Cl.
CPC ............ *A61B 18/1492* (2013.01); *A61N 7/02* (2013.01); *A61B 2018/0016* (2013.01);
(Continued)

(58) Field of Classification Search
CPC ........ A61B 18/1492; A61B 2018/0016; A61B 2018/00214; A61B 2018/00267;
(Continued)

(56) References Cited

U.S. PATENT DOCUMENTS 4,602,624 A 7/1986 Naples et al.
4,649,936 A 3/1987 Ungar et al.
(Continued)

FOREIGN PATENT DOCUMENTS

CN 2855350 1/2007
CN 102274074 12/2011
(Continued)

OTHER PUBLICATIONS

Opposition to European Patent No. EP0930979, Published Jul. 28, 1999, Decision Dated Sep. 12, 2012, 28 pages.
(Continued)

*Primary Examiner* — Daniel W Fowler
*Assistant Examiner* — Tigist S Demie
(74) *Attorney, Agent, or Firm* — Medtronic Vascular, Inc. IP Legal Department

(57) ABSTRACT

Catheters including elements configured to deliver energy to nerves at or near a treatment location within a body lumen. A treatment assembly is transformable between a low-profile delivery configuration wherein a pair of electrodes are in a staggered arrangement relative to each other along the longitudinal axis, and an expanded deployed configuration wherein the pair of electrodes is aligned along an electrode axis that is orthogonal relative to the longitudinal axis.

7 Claims, 10 Drawing Sheets

(51) Int. Cl.
*A61B 18/00* (2006.01)
*A61M 25/00* (2006.01)
*A61N 1/20* (2006.01)
*A61N 7/00* (2006.01)

(52) U.S. Cl.
CPC .............. *A61B 2018/00214* (2013.01); *A61B 2018/00267* (2013.01); *A61B 2018/00404* (2013.01); *A61B 2018/00434* (2013.01); *A61B 2018/00511* (2013.01); *A61B 2018/00577* (2013.01); *A61B 2018/00642* (2013.01); *A61B 2018/1407* (2013.01); *A61B 2018/1467* (2013.01); *A61M 25/0084* (2013.01); *A61N 1/205* (2013.01); *A61N 2007/003* (2013.01); *A61N 2007/0026* (2013.01)

(58) Field of Classification Search
CPC ........... A61B 2018/00404; A61B 2018/00434; A61B 2018/00511; A61B 2018/00577; A61B 2018/00642; A61B 2018/1407; A61B 2018/1467; A61M 25/0084; A61N 1/205; A61N 2007/0026; A61N 2007/003; A61N 7/02
See application file for complete search history.

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,976,711 A | 12/1990 | Parins et al. |
| 5,078,717 A | 1/1992 | Parins et al. |
| 5,190,540 A | 3/1993 | Lee |
| 5,300,068 A | 4/1994 | Rosar et al. |
| 5,304,120 A | 4/1994 | Crandell et al. |
| 5,345,936 A | 9/1994 | Pomeranz et al. |
| 5,358,514 A | 10/1994 | Schulman et al. |
| 5,368,591 A | 11/1994 | Lennox et al. |
| 5,423,744 A | 6/1995 | Gencheff et al. |
| 5,425,364 A | 6/1995 | Imran |
| 5,465,717 A | 11/1995 | Imran et al. |
| 5,476,495 A | 12/1995 | Kordis et al. |
| 5,484,400 A | 1/1996 | Edwards et al. |
| 5,496,311 A | 3/1996 | Abele et al. |
| 5,540,679 A | 7/1996 | Fram et al. |
| 5,571,147 A | 11/1996 | Sluijter et al. |
| 5,599,345 A | 2/1997 | Edwards et al. |
| 5,626,576 A | 5/1997 | Janssen |
| 5,636,634 A | 6/1997 | Kordis et al. |
| 5,672,174 A | 9/1997 | Gough et al. |
| 5,688,266 A | 11/1997 | Edwards et al. |
| 5,700,282 A | 12/1997 | Zabara |
| 5,704,908 A | 1/1998 | Hofmann et al. |
| 5,707,400 A | 1/1998 | Terry, Jr. et al. |
| 5,722,401 A | 3/1998 | Pietroski et al. |
| 5,772,590 A | 6/1998 | Webster, Jr. |
| 5,807,306 A | 9/1998 | Shapland et al. |
| 5,860,974 A | 1/1999 | Abele |
| 5,865,787 A | 2/1999 | Shapland et al. |
| 5,893,885 A | 4/1999 | Webster et al. |
| 5,944,710 A | 8/1999 | Dev et al. |
| 5,954,719 A | 9/1999 | Chen et al. |
| 5,954,742 A | 9/1999 | Osypka |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,066,134 A | 5/2000 | Eggers et al. |
| 6,099,524 A | 8/2000 | Lipson et al. |
| 6,117,101 A | 9/2000 | Diederich et al. |
| 6,135,999 A | 10/2000 | Fanton et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,488,679 B1 | 12/2002 | Swanson et al. |
| 6,500,174 B1 | 12/2002 | Maguire et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,562,034 B2 | 5/2003 | Edwards et al. |
| 6,575,933 B1 | 6/2003 | Wittenberger et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,673,090 B2 | 1/2004 | Root et al. |
| 6,679,268 B2 | 1/2004 | Stevens et al. |
| 6,685,648 B2 | 2/2004 | Flaherty et al. |
| 6,692,490 B1 | 2/2004 | Edwards |
| 6,695,830 B2 | 2/2004 | Vigil et al. |
| 6,736,835 B2 | 5/2004 | Pellegrino et al. |
| 6,748,255 B2 | 6/2004 | Fuimaono et al. |
| 6,748,954 B2 | 6/2004 | Sherry et al. |
| 6,749,607 B2 | 6/2004 | Edwards et al. |
| 6,752,805 B2 | 6/2004 | Maguire et al. |
| 6,763,261 B2 | 7/2004 | Casscells, III et al. |
| 6,780,183 B2 | 8/2004 | Jimenez, Jr. et al. |
| 6,829,497 B2 | 12/2004 | Mogul |
| 6,837,886 B2 | 1/2005 | Collins et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,917,834 B2 | 7/2005 | Koblish et al. |
| 6,923,808 B2 | 8/2005 | Taimisto |
| 6,939,346 B2 | 9/2005 | Kannenberg et al. |
| 6,949,097 B2 | 9/2005 | Stewart et al. |
| 6,974,456 B2 | 12/2005 | Edwards et al. |
| 7,022,105 B1 | 4/2006 | Edwards |
| 7,100,614 B2 | 9/2006 | Stevens et al. |
| 7,104,987 B2 | 9/2006 | Biggs et al. |
| 7,149,574 B2 | 12/2006 | Yun et al. |
| 7,162,303 B2 | 1/2007 | Levin et al. |
| 7,221,979 B2 | 5/2007 | Zhou et al. |
| 7,291,146 B2 | 11/2007 | Steinke et al. |
| 7,381,200 B2 | 6/2008 | Katoh et al. |
| 7,390,894 B2 | 6/2008 | Weinshilboum et al. |
| 7,532,938 B2 | 5/2009 | Machado et al. |
| 7,617,005 B2 | 11/2009 | Demarais et al. |
| 7,647,115 B2 | 1/2010 | Levin et al. |
| 7,653,438 B2 | 1/2010 | Deem et al. |
| 7,678,123 B2 | 3/2010 | Chanduszko |
| 7,717,948 B2 | 5/2010 | Demarais et al. |
| 7,778,703 B2 | 8/2010 | Gross et al. |
| 7,850,685 B2 | 12/2010 | Kunis et al. |
| 8,007,495 B2 | 8/2011 | McDaniel et al. |
| 8,019,435 B2 | 9/2011 | Hastings et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,295,902 B2 | 10/2012 | Salahieh et al. |
| 8,337,492 B2 | 12/2012 | Kunis et al. |
| 8,584,681 B2 | 11/2013 | Danek et al. |
| 8,909,316 B2 | 12/2014 | Ng |
| 8,951,251 B2 | 2/2015 | Willard |
| 8,979,839 B2 | 3/2015 | De La Rama et al. |
| 9,173,696 B2 | 11/2015 | Schauer et al. |

(56) References Cited

U.S. PATENT DOCUMENTS

| | | |
|---|---|---|
| 9,414,885 B2 | 8/2016 | Willard |
| 2001/0044596 A1 | 11/2001 | Jaafar |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050637 A1 | 3/2003 | Maguire et al. |
| 2003/0050681 A1 | 3/2003 | Pianca et al. |
| 2003/0060820 A1 | 3/2003 | Maguire et al. |
| 2003/0060858 A1 | 3/2003 | Kieval et al. |
| 2003/0074039 A1 | 4/2003 | Puskas |
| 2003/0125790 A1 | 7/2003 | Fastovsky et al. |
| 2003/0144658 A1 | 7/2003 | Schwartz et al. |
| 2003/0158584 A1 | 8/2003 | Cates et al. |
| 2003/0176816 A1 | 9/2003 | Maguire et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2003/0233099 A1 | 12/2003 | Danaek et al. |
| 2003/0236455 A1 | 12/2003 | Swanson et al. |
| 2004/0010289 A1 | 1/2004 | Biggs et al. |
| 2004/0082978 A1 | 4/2004 | Harrison et al. |
| 2004/0215186 A1 | 10/2004 | Cornelius et al. |
| 2005/0033137 A1 | 2/2005 | Oral et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0228460 A1 | 10/2005 | Levin et al. |
| 2006/0095029 A1 | 5/2006 | Young et al. |
| 2006/0100618 A1 | 5/2006 | Chan et al. |
| 2006/0206150 A1 | 9/2006 | Demarais et al. |
| 2006/0247618 A1 | 11/2006 | Kaplan et al. |
| 2006/0247619 A1 | 11/2006 | Kaplan et al. |
| 2006/0271111 A1 | 11/2006 | Demarais et al. |
| 2007/0083194 A1 | 4/2007 | Kunis et al. |
| 2007/0106293 A1 | 5/2007 | Oral et al. |
| 2007/0129720 A1 | 6/2007 | Demarais et al. |
| 2007/0265687 A1 | 11/2007 | Deem et al. |
| 2007/0287994 A1 | 12/2007 | Patel |
| 2008/0319513 A1 | 12/2008 | Pu et al. |
| 2009/0024195 A1 | 1/2009 | Rezai et al. |
| 2009/0036948 A1 | 2/2009 | Levin et al. |
| 2009/0076409 A1 | 3/2009 | Wu et al. |
| 2010/0023088 A1 | 1/2010 | Stack et al. |
| 2010/0137860 A1 | 6/2010 | Demarais et al. |
| 2010/0137952 A1 | 6/2010 | Demarais et al. |
| 2010/0168737 A1 | 7/2010 | Grunewald |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2010/0286684 A1 | 11/2010 | Hata et al. |
| 2011/0118726 A1 | 5/2011 | De La Rama et al. |
| 2011/0213231 A1 | 9/2011 | Hall et al. |
| 2011/0257622 A1 | 10/2011 | Salahieh et al. |
| 2011/0301587 A1 | 12/2011 | Deem et al. |
| 2011/0306851 A1 | 12/2011 | Wang |
| 2012/0029500 A1 | 2/2012 | Jenson |
| 2012/0029504 A1 | 2/2012 | Afonso et al. |
| 2012/0029510 A1 | 2/2012 | Haverkost |
| 2012/0071870 A1 | 3/2012 | Salahieh et al. |
| 2012/0130289 A1 | 5/2012 | Demarais et al. |
| 2012/0130345 A1 | 5/2012 | Levin et al. |
| 2012/0157992 A1 | 6/2012 | Smith et al. |
| 2012/0157993 A1 | 6/2012 | Jenson et al. |
| 2012/0172837 A1 | 7/2012 | Demarais et al. |
| 2012/0172859 A1 | 7/2012 | Condie et al. |
| 2012/0184952 A1 | 7/2012 | Jenson et al. |
| 2012/0265198 A1 | 10/2012 | Crow et al. |
| 2012/0296232 A1 | 11/2012 | Ng |
| 2012/0296329 A1 | 11/2012 | Ng |
| 2013/0053732 A1 | 2/2013 | Heuser |
| 2013/0090651 A1 | 4/2013 | Smith |
| 2013/0090652 A1 | 4/2013 | Jenson |
| 2013/0096550 A1 | 4/2013 | Hill |
| 2013/0096554 A1 | 4/2013 | Groff et al. |
| 2013/0110106 A1 | 5/2013 | Richardson |
| 2013/0116687 A1 | 5/2013 | Willard |
| 2013/0123778 A1 | 5/2013 | Richardson et al. |
| 2013/0158509 A1 | 6/2013 | Consigny et al. |
| 2013/0158536 A1 | 6/2013 | Bloom |
| 2013/0226166 A1 | 8/2013 | Chomas et al. |
| 2013/0231658 A1 | 9/2013 | Wang et al. |
| 2013/0231659 A1* | 9/2013 | Hill .................. A61B 18/1492 606/41 |
| 2013/0245622 A1 | 9/2013 | Wang et al. |
| 2013/0253623 A1 | 9/2013 | Danek et al. |
| 2013/0274614 A1 | 10/2013 | Shimada et al. |
| 2013/0282000 A1 | 10/2013 | Parsonage |
| 2013/0282084 A1 | 10/2013 | Mathur et al. |
| 2013/0289369 A1 | 10/2013 | Margolis |
| 2013/0289555 A1 | 10/2013 | Mayse et al. |
| 2013/0289556 A1 | 10/2013 | Mayse et al. |
| 2013/0289686 A1 | 10/2013 | Masson et al. |
| 2014/0012253 A1 | 1/2014 | Mathur |
| 2014/0018789 A1 | 1/2014 | Kaplan et al. |
| 2014/0018790 A1 | 1/2014 | Kaplan et al. |
| 2014/0025063 A1 | 1/2014 | Kaplan et al. |
| 2014/0025069 A1 | 1/2014 | Willard et al. |
| 2014/0046319 A1 | 2/2014 | Danek et al. |
| 2014/0074083 A1 | 3/2014 | Horn et al. |
| 2014/0074089 A1 | 3/2014 | Nishii |
| 2014/0107639 A1 | 4/2014 | Zhang et al. |
| 2014/0142408 A1 | 5/2014 | De La Rama et al. |
| 2014/0188103 A1 | 7/2014 | Millett |
| 2014/0207136 A1 | 7/2014 | De La Rama et al. |
| 2014/0246465 A1 | 9/2014 | Peterson et al. |
| 2014/0276124 A1 | 9/2014 | Cholette et al. |
| 2014/0276724 A1 | 9/2014 | Goshayeshgar |
| 2014/0276728 A1 | 9/2014 | Goshayeshgar |
| 2014/0276733 A1 | 9/2014 | VanScoy et al. |
| 2014/0276742 A1 | 9/2014 | Nabutovsky et al. |
| 2014/0276752 A1 | 9/2014 | Wang et al. |
| 2014/0276762 A1 | 9/2014 | Parsonage |
| 2014/0276766 A1 | 9/2014 | Brotz et al. |
| 2014/0276767 A1 | 9/2014 | Brotz et al. |
| 2014/0276773 A1 | 9/2014 | Brotz et al. |
| 2014/0296849 A1 | 10/2014 | Coe et al. |
| 2014/0316400 A1 | 10/2014 | Blix et al. |
| 2014/0316496 A1 | 10/2014 | Masson et al. |
| 2014/0330267 A1 | 11/2014 | Harrington |
| 2014/0350553 A1 | 11/2014 | Okuyama |
| 2014/0364926 A1 | 12/2014 | Nguyen et al. |
| 2015/0018656 A1 | 1/2015 | Min et al. |
| 2015/0018818 A1 | 1/2015 | Willard et al. |
| 2015/0105715 A1 | 4/2015 | Pikus et al. |
| 2015/0105772 A1 | 4/2015 | Hill et al. |
| 2015/0112327 A1 | 4/2015 | Willard |
| 2015/0112329 A1 | 4/2015 | Ng |
| 2015/0148797 A1 | 5/2015 | Willard |
| 2015/0223866 A1 | 8/2015 | Buelna et al. |
| 2015/0289770 A1 | 10/2015 | Wang |
| 2015/0351836 A1 | 12/2015 | Prutchi |
| 2015/0374435 A1 | 12/2015 | Cao et al. |
| 2016/0008059 A1 | 1/2016 | Prutchi |
| 2016/0324574 A1 | 11/2016 | Willard |
| 2016/0374568 A1 | 12/2016 | Wang |

FOREIGN PATENT DOCUMENTS

| | | |
|---|---|---|
| CN | 202069688 | 12/2011 |
| CN | 202426647 | 9/2012 |
| CN | 102885648 | 1/2013 |
| CN | 102885649 | 1/2013 |
| CN | 102908188 | 2/2013 |
| CN | 102908189 | 2/2013 |
| CN | 202761434 | 3/2013 |
| CN | 202843784 | 4/2013 |
| CN | 202960760 | 6/2013 |
| DE | 29909082 | 7/1999 |
| DE | 10252325 | 5/2004 |
| DE | 10257146 | 6/2004 |
| DE | 20 2004 021 941 | 5/2013 |
| DE | 20 2004 021 942 | 5/2013 |
| DE | 20 2004 021 949 | 5/2013 |
| DE | 20 2004 021 951 | 6/2013 |

(56) References Cited

FOREIGN PATENT DOCUMENTS

| | | |
|---|---|---|
| DE | 20 2004 021 952 | 6/2013 |
| DE | 20 2004 021 953 | 6/2013 |
| DE | 20 2004 021 944 | 7/2013 |
| EP | 1180004 | 2/2002 |
| EP | 1634542 | 3/2006 |
| EP | 1802370 | 7/2007 |
| EP | 1874211 | 1/2008 |
| EP | 1009303 | 6/2009 |
| EP | 2429436 | 3/2012 |
| EP | 2457615 A1 | 5/2012 |
| EP | 2498706 | 9/2012 |
| EP | 25191732 | 11/2012 |
| EP | 25580162 | 2/2013 |
| EP | 2598068 | 6/2013 |
| EP | 2598069 | 6/2013 |
| EP | 2640297 | 9/2013 |
| EP | 2709517 A1 | 3/2014 |
| EP | 2717795 | 4/2014 |
| EP | 2457615 B1 | 12/2014 |
| EP | 2819604 A1 | 1/2015 |
| EP | 2874555 A1 | 5/2015 |
| EP | 2895095 A2 | 7/2015 |
| EP | 2950734 A2 | 12/2015 |
| EP | 2954865 A1 | 12/2015 |
| EP | 2967383 A1 | 1/2016 |
| EP | 3011899 A1 | 4/2016 |
| EP | 3019105 A1 | 5/2016 |
| EP | 3102132 A1 | 12/2016 |
| JP | 2016083302 | 5/2016 |
| JP | 2016086999 | 5/2016 |
| WO | WO-199202029 | 2/1992 |
| WO | WO-199211898 | 7/1992 |
| WO | WO-9421165 | 9/1994 |
| WO | WO-9421168 | 9/1994 |
| WO | WO-199510319 | 4/1995 |
| WO | WO-1995025472 | 9/1995 |
| WO | WO-199634559 | 11/1996 |
| WO | WO-199717892 | 5/1997 |
| WO | WO-1997036548 | 10/1997 |
| WO | WO-1999/00060 | 1/1999 |
| WO | WO-9900060 | 1/1999 |
| WO | WO 1999044522 | 9/1999 |
| WO | WO-199952424 | 10/1999 |
| WO | WO-1999062413 | 12/1999 |
| WO | WO-2000062699 | 10/2000 |
| WO | WO-2001022897 | 4/2001 |
| WO | WO-2001070114 | 9/2001 |
| WO | WO-2003/082080 | 10/2003 |
| WO | WO 2005001513 | 1/2005 |
| WO | WO-2005041748 | 5/2005 |
| WO | WO-20050417482 | 5/2005 |
| WO | WO-2005110528 | 11/2005 |
| WO | WO 2006009376 | 1/2006 |
| WO | WO-2006041881 | 4/2006 |
| WO | WO-20060418812 | 4/2006 |
| WO | WO-2007008954 | 1/2007 |
| WO | WO-2010056771 | 5/2010 |
| WO | WO-2011/060200 | 5/2011 |
| WO | WO 2011055143 | 5/2011 |
| WO | WO2011060339 | 5/2011 |
| WO | WO-20110822792 | 7/2011 |
| WO | WO-20111198572 | 9/2011 |
| WO | WO-20111305342 | 10/2011 |
| WO | WO-2012068471 | 5/2012 |
| WO | WO-2012075156 | 6/2012 |
| WO | WO-2012130337 | 10/2012 |
| WO | WO-2012131107 | 10/2012 |
| WO | WO-2012158864 | 11/2012 |
| WO | WO-2012170482 | 12/2012 |
| WO | WO2013022853 | 2/2013 |
| WO | WO-2013028812 | 2/2013 |
| WO | WO-2013055815 | 4/2013 |
| WO | WO-2013070724 | 5/2013 |
| WO | WO-2013077283 | 5/2013 |
| WO | WO-20131060542 | 7/2013 |
| WO | WO-20131128442 | 8/2013 |
| WO | WO-2013/142217 | 9/2013 |
| WO | WO-2013131046 | 9/2013 |
| WO | WO-2013165920 | 11/2013 |
| WO | WO-2014015065 | 1/2014 |
| WO | WO-2014150204 | 9/2014 |
| WO | WO-2014150425 | 9/2014 |
| WO | WO-2014150432 | 9/2014 |
| WO | WO-2014150441 | 9/2014 |
| WO | WO-2014150455 | 9/2014 |
| WO | WO-2014163990 | 10/2014 |
| WO | WO-2014179768 | 11/2014 |
| WO | WO-2014197688 | 12/2014 |

OTHER PUBLICATIONS

U.S. Appl. No. 95/002,253, Office Action dated Oct. 23, 2013, 24 pages.
U.S. Appl. No. 60/616,254, "Renal neuromodulation", filed Oct. 5, 2004, 25 pages.
U.S. Appl. No. 60/624,793, "Renal neuromodulation", filed Nov. 2, 2004, 20 pages.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hemaluria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361;9.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimentla Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009.
Schlaich, M.P. et al., "Renal Denervation as a Therapeutic Approach for Hypertension: Novel Implictions for an Old Concept," Hypertension, 2009; 54:1195-1201.

(56) References Cited

OTHER PUBLICATIONS

Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16:160.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
European Search Report for European Application No. 13159256, dated Oct. 17, 2013, 6 pages.
Eick, Olaf, "Temperature Controlled Radiofrequency Ablation." Indian Pacing and Electrophysiology Journal, vol. 2. No. 3, 2002, 8 pages.
European Search Report dated Feb. 22, 2013; Application No. 12180432.2; Applicant: Medtronic Ardian Luxembourg S.a.r.l.; 6 pages.
European Search Report dated Feb. 28, 2013; Application No. 12180427.2; Applicant: Medtronic Ardian Luxembourg S.a.r.l.; 4 pages.
European Search Report dated May 3, 2012; European Patent Application No. 11192511.1; Applicant: Ardian, Inc. (6 pages).
European Search Report dated May 3, 2012; European Patent Application No. 11192514.5; Applicant: Ardian, Inc. (7 pages).
European Search Report dated Jan. 30, 2013; Application No. 12180428.0; Applicant: Medtronic Ardian Luxembourg S.a.r.l.; 6 pages.
European Search Report dated Jan. 30, 2013; Application No. 12180430.6; Applicant: Medtronic Ardian Luxembourg S.a.r.l.; 6 pages.
European Search Report dated Jan. 30, 2013; Application No. 12180431.4; Applicant: Medtronic Ardian Luxembourg S.a.r.l.; 6 pages.
European Search Report dated Jan. 30, 2013; European Application No. 12180426.4; Applicant: Medtronic Ardian Luxembourg S.a.r.l.; 6 pages.
Extended European Search Report for European Patent Application No. 15158850.6, dated Aug. 18, 2015, 7 pages.
Mount Sinai School of Medicine clinical trial for Impact of Renal Sympathetic Denervation of Chronic Hypertension, Mar. 2013, 11 pages. http://clinicaltrials.go.8 . . . .
Prochnau, Dirk et al., Catheter-based renal denervation for drug-resistant hypertension by using a standard electrophysiology catheter; Euro Intervention 2012, vol. 7, pp. 1077-1080.
ThermoCool Irrigated Catheter and Integrated Ablation System, Biosense Webster (2006), 6 pages.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news-latest---news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n. l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced Its Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.

(56) References Cited

OTHER PUBLICATIONS

Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.

Davis, Mark et al., "Effectiveness of Renal Denervation Therapy for Resistant Hypertension." Journal of the American College of Cardiology, vol. 62, No. 3, 2013, 11 pages.

Dibona, G.F. "Sympathetic nervous system and kidney in hypertension." Nephrol and Hypertension, 11: 197-200 (2002).

Dubuc, M., et al., "Feasibility of cardiac cryoablation using a transvenous steerable electrode catheter." J Intery Cardiac Electrophysiol, 2:285-292 (1998).

Final Office Action; U.S. Appl. No. 12/827,700; dated Feb. 5, 2013, 61 pages.

Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.

Gelfand, M., et al., "Treatment of renal failure and hypertension." U.S. Appl. No. 60/442,970, filed Jan. 29, 2003, 23 pages.

Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).

Hall, W. H., et al. "Combined embolization and percutaneous radiofrequency ablation of a solid renal tumor." *Am. J. Roentgenol*,174: 1592-1594 (2000).

Han, Y.-M, et al., "Renal artery ebolization with diluted hot contrast medium: An experimental study." J Vasc Intery Radiol, 12: 862-868 (2001).

Hansen, J. M., et al. "The transplanted human kidney does not achieve functional reinnervation." *Clin. Sci*, 87: 13-19 (1994).

Hendee, W. R. et al. "Use of Animals in Biomedical Research: The Challenge and Response." *American Medical Association White Paper* (1988) 39 pages.

Hering, Dagmara et al., "Chronic kidney disease: role of sympathetic nervous system activation and potential benefits of renal denervation." EuroIntervention, vol. 9, 2013, 9 pages.

Huang et al., "Renal denervation prevents and reverses hyperinsulinemia-induced hypertension in rats." Hypertension 32 (1998) pp. 249-254.

Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.

Kaiser, Chris, AHA Lists Year's Big Advances in CV Research, medpage Today, Dec. 18, 2012, 4 pages, <http://www.medpagetoday.com/Cardiology/PCI/36509>.

Kompanowska, E., et al., "Early Effects of renal denervation in the anaesthetised rat: Natriuresis and increased cortical blood flow." J Physiol, 531. 2:527-534 (2001).

Lee, S.J., et al. "Ultrasonic energy in endoscopic surgery." Yonsei Med J, 40:545-549 (1999).

Linz, Dominik et al., "Renal denervation suppresses ventricular arrhythmias during acute ventricular ischemia in pigs." Heart Rhythm, vol. 0, No. 0, 2013, 6 pages.

Lustgarten, D.L.,et al., "Cryothermal ablation: Mechanism of tissue injury and current experience in the treatment of tachyarrhythmias." Progr Cardiovasc Dis, 41:481-498 (1999).

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

Mahfoud, Felix et al., "Expert consensus document from the European Society of Cardiology on catheter-based renal denervation." European Heart Journal, 2013, 9 pages.

Mahfoud, Felix et al., "Renal Hemodynamics and Renal Function After Catheter-Based Renal Sympathetic Denervation in Patients With Resistant Hypertension." Hypertension, 2012, 6 pages.

Medical-Dictionary.com, Definition of "Animal Model," http://medical-dictionary.com (search "Animal Model"), 2005, 1 page.

Medtronic, Inc., Annual Report (Form 10-K) (Jun. 28, 2011) 44 pages.

Millard, F. C., et al, "Renal Embolization for ablation of function in renal failure and hypertension." Postgraduate Medical Journal, 65, 729-734, (1989).

Oliveira, V., et al., "Renal denervation normalizes pressure and baroreceptor reflex in high renin hypertension in conscious rats." Hypertension, 19:II-17-II-21 (1992).

Ong, K. L., et al. "Prevalence, Awareness, Treatment, and Control of Hypertension Among United States Adults 1999-2004." Hypertension, 49: 69-75 (2007) (originally published online Dec. 11, 2006).

Ormiston, John et al., "First-in-human use of the OneShot$^{TM}$ renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Peet, M., "Hypertension and its Surgical Treatment by bilateral supradiaphragmatic splanchnicectomy" Am J Surgery (1948) pp. 48-68.

Renal Denervation (RDN), Symplicity RDN System Common Q&A (2011), 4 pages, http://www.medtronic.com/rdn/mediakit/RDN%20FAQ.pdf.

Schauerte, P., et al. "Catheter ablation of cardiac autonomic nerves for prevention of vagal atrial fibrillation." Circulation, 102:2774-2780 (2000).

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated ESH position paper on interventional therapy of resistant hypertension." EuroIntervention, vol. 9, 2013, 9 pages.

Sievert, Horst, "Novelty Award EuroPCR 2010." Euro PCR, 2010, 15 pages.

Solis-Herruzo et al., "Effects of lumbar sympathetic block on kidney function in cirrhotic patients with hepatorenal syndrome," J. Hepatol. 5 (1987), pp. 167-173.

Stella, A., et al., "Effects of reversible renal denervation on haemodynamic and excretory functions on the ipsilateral and contralateral kidney in the cat." Hypertension, 4:181-188 (1986).

Stouffer, G. A. et al., Journal of Molecular and Cellular Cardiology, vol. 62, 2013, 6 pages.

Swartz, J. F., et al., "Radiofrequency endocardial catheter ablation of accessory atrioventricular pathway atrial insertion sites." Circulation, 87: 487-499 (1993).

Uchida, F., et al., "Effect of radiofrequency catheter ablation on parasympathetic denervation: A comparison of three different ablation sites." PACE, 21:2517-2521 (1998).

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.

(56) References Cited

OTHER PUBLICATIONS

Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005, (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 : 484-490, 2005.
Schneider, Peter A., "Endovascular Skills—Guidewire and Catheter Skills for Endovascular Surgery," Second Edition Revised and Expanded, 10 pages, (2003).
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.

\* cited by examiner

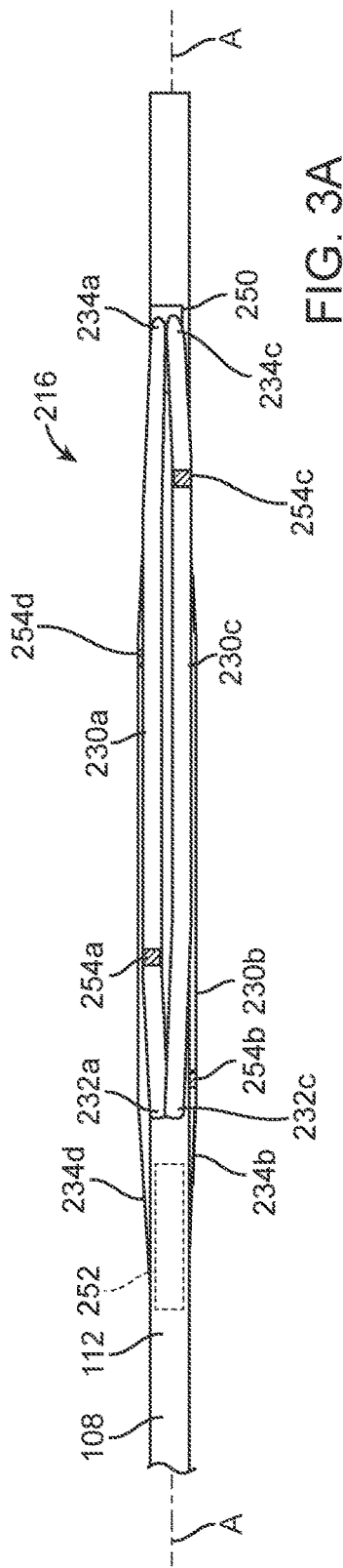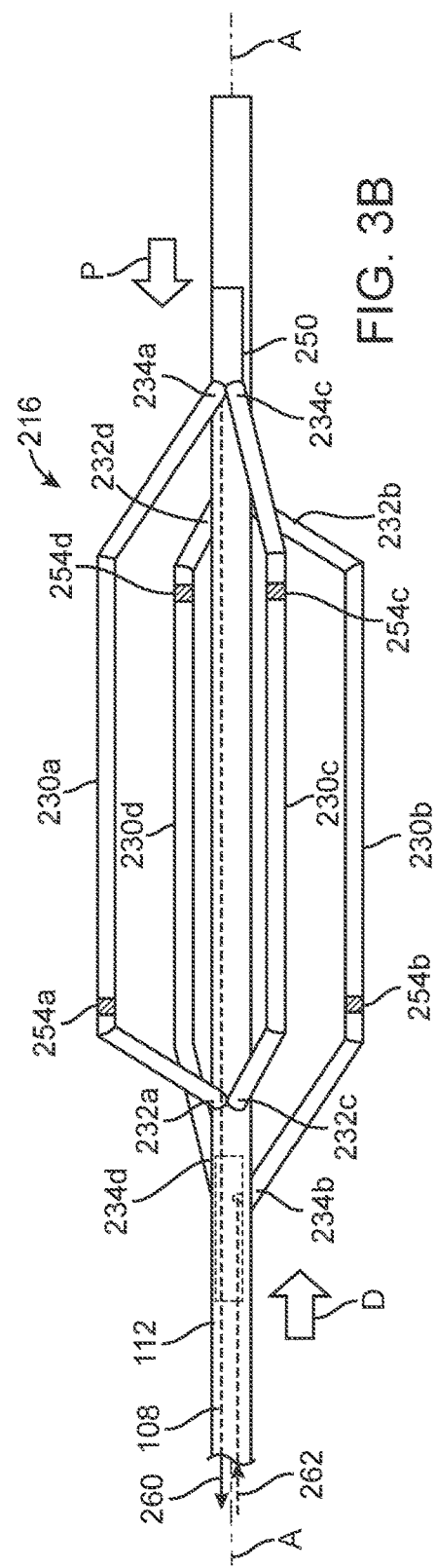

LOW PROFILE CATHETER ASSEMBLIES AND ASSOCIATED SYSTEMS AND METHODS

CROSS-REFERENCE TO RELATED APPLICATIONS

The present application is a divisional of U.S. patent application Ser. No. 14/208,769, filed Mar. 13, 2014 (published as U.S. Patent Publication US 2015/0257825 A1 on Sep. 17, 2015).

TECHNICAL FIELD

The present technology is related to catheters. In particular, at least some embodiments are related to low profile neuromodulation catheters including energy delivery elements configured to deliver energy to nerves at or near a treatment location within a body lumen.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS, in particular, has been identified experimentally and in humans as a likely contributor to the complex pathophysiologies of hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

In FIG. 2A, the treatment assembly is shown in a low-profile delivery configuration. In FIGS. 2B and 2C, the treatment assembly is shown in an expanded deployed configuration.

FIGS. 3A-3C are enlarged views of a treatment assembly of a catheter configured in accordance with another embodiment of the present technology. In FIG. 3A, the treatment assembly is shown in a low-profile delivery configuration. In FIGS. 3B and 3C, the treatment assembly is shown in an expanded deployed configuration.

In FIG. 6A, a delivery sheath is inserted into a renal artery. In FIG. 6B, the treatment assembly is shown extended from the sheath in an intermediate state. In FIG. 6C, the treatment assembly is shown in the deployed state.

DETAILED DESCRIPTION

Figure 1:
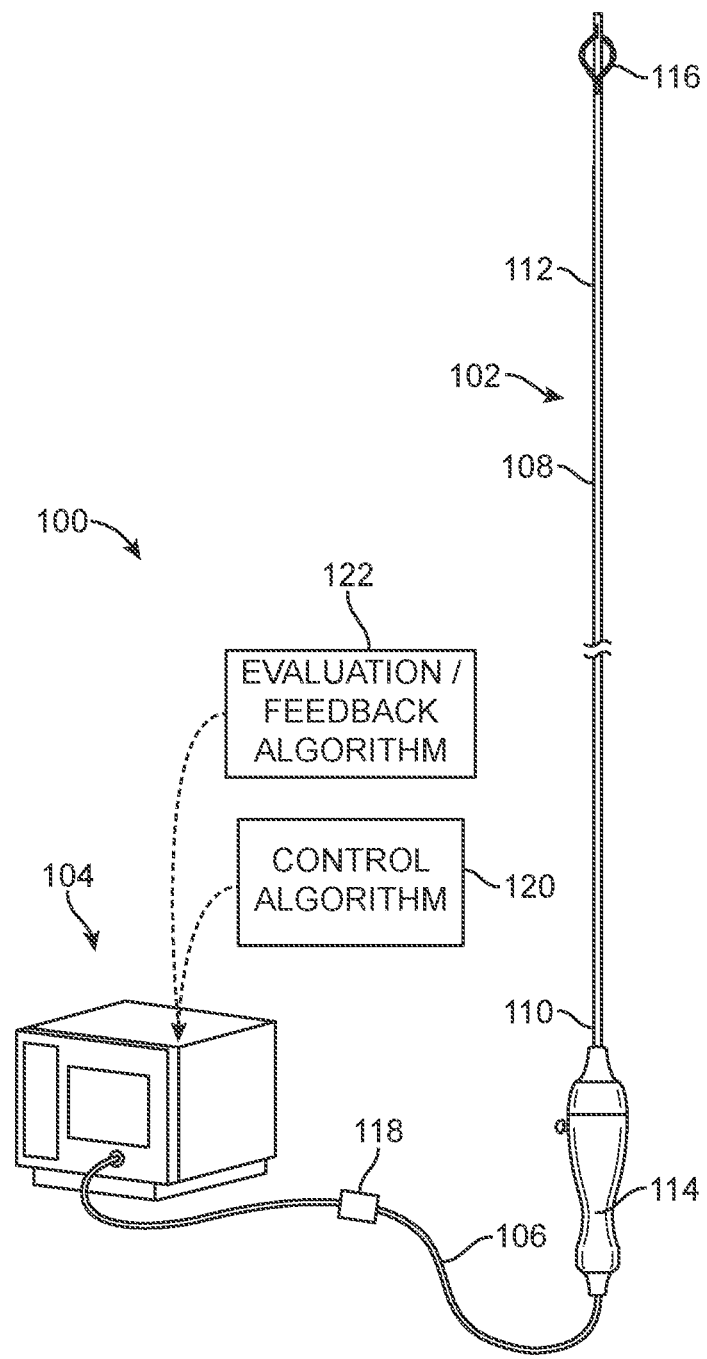
FIG. 1 is a perspective view of a system including a catheter, console, and cable configured in accordance with an embodiment of the present technology. The catheter includes an elongated shaft and a treatment assembly carried by the shaft.

The present technology is related to catheters, such as low profile neuromodulation catheters with independent expansion members carrying energy delivery elements configured to deliver energy to nerves at or near a treatment location within a body lumen. Embodiments of the present technology, for example, are directed to catheters having energy delivery elements arranged in a staggered or misaligned arrangement when the catheter is in a low-profile delivery configuration. In this way, the energy delivery elements are not overlapping when the catheter is in a low-profile delivery configuration, which is expected to reduce the overall profile of the catheter. Further, when the energy delivery elements are at a desired treatment site within the patient, the treatment assembly is transformable to an expanded, deployed arrangement such that the energy delivery elements are aligned relative to each other (e.g., lie in a plane that is orthogonal relative to a longitudinal axis of the catheter) and are positioned to produce a desired ablation pattern in target tissue.

Neuromodulation catheters configured in accordance with embodiments of the present technology can include, for example, an elongated tubular shaft extending along a longitudinal axis. The elongated shaft includes a proximal portion and a distal portion. The catheter can also include a treatment assembly at the distal portion of the shaft and configured to be located at a target location within a blood vessel of a human patient. The treatment assembly includes a pair of electrodes. The treatment assembly is transformable between (a) a low-profile delivery configuration wherein the pair of electrodes are in a staggered arrangement relative to each other along the longitudinal axis, and (b) an expanded deployed configuration wherein the pair of electrodes are aligned along an electrode axis that is orthogonal relative to the longitudinal axis.

Specific details of several embodiments of the present technology are described herein with reference to FIGS. 1-6C. Although many of the embodiments are described herein with respect to devices, systems, and methods for percutaneous intravascular renal neuromodulation, other clinical applications and other embodiments in addition to those described herein are within the scope of the present technology. For example, at least some embodiments may be useful for neuromodulation within a body lumen other than a blood vessel, for non-renal neuromodulation, and/or for use in therapies other than neuromodulation. It should be noted that other embodiments in addition to those disclosed herein are within the scope of the present technology. Furthermore, embodiments of the present technology can have different configurations and components, and may be used for procedures different from those disclosed herein. Moreover, a person of ordinary skill in the art will understand that embodiments of the present technology can have configurations, components, and/or procedures in addition to those disclosed herein and that these and other embodiments can be without several of the configurations, components, and/or procedures disclosed herein without deviating from the present technology.

As used herein, the terms "distal" and "proximal" define a position or direction with respect to a clinician or a clinician's control device (e.g., a handle of a catheter). The terms, "distal" and "distally" refer to a position distant from or in a direction away from a clinician or a clinician's control device. The terms "proximal" and "proximally" refer to a position near or in a direction toward a clinician or a clinician's control device. The headings provided herein are for convenience only and should not be construed as limiting the subject matter disclosed.

Selected Examples of Neuromodulation Catheters and Related Devices

FIG. 1 is a perspective view of a system 100 (e.g., a neuromodulation system) configured in accordance with an embodiment of the present technology. The system 100 can include a catheter 102 (e.g., a neuromodulation catheter), a console 104, and a cable 106 extending therebetween. The catheter 102 can include an elongate shaft 108 having a proximal end portion 110 and a distal end portion 112. The catheter 102 can further include a handle 114 and a treatment or therapeutic assembly 116 operably connected to the shaft 108 via, respectively, the proximal and distal end portions 110, 112 of the shaft 108. The shaft 108 can be configured to intravascularly locate the treatment assembly 116 at a treatment location within a body lumen, such as a suitable blood vessel, duct, airway, or other naturally occurring lumen within the human body. The treatment assembly 116 can be configured to provide or support therapy (e.g., a neuromodulation treatment) at the treatment location.

The treatment assembly 116 may be configured to be radially constrained and slidably disposed within a delivery sheath (not shown) while the catheter 102 is being deployed within a body lumen. The outside diameter of the sheath can be 5, 6, or 7 French or another suitable size. As another example, the catheter 102 can be steerable or non-steerable and configured for deployment without a guide wire. The catheter 102 can also be configured for deployment via a guide catheter (not shown) with or without the use of a delivery sheath or a guide wire.

The console 104 can be configured to control, monitor, supply energy, and/or otherwise support operation of the catheter 102. Alternatively, the catheter 102 can be self-contained or otherwise configured for operation without connection to a console 104. When present, the console 104 can be configured to generate a selected form and/or magnitude of energy for delivery to tissue at or near a treatment location via the treatment assembly 116. The console 104 can have different configurations depending on the treatment modality of the catheter 102. When the catheter 102 is configured for electrode-based, heat-element-based, or transducer-based treatment, for example, the console 104 can include an energy generator (not shown) configured to generate radio frequency (RF) energy (e.g., monopolar and/or bipolar RF energy), pulsed electrical energy, microwave energy, ultrasound energy (e.g., intravascularly delivered ultrasound energy, high-intensity focused ultrasound energy), direct heat, electromagnetic radiation (e.g., infrared, visible, and/or gamma radiation), and/or another suitable type of energy. Similarly, when the catheter 102 is configured for chemical-based treatment (e.g., drug infusion), the console 104 can include a chemical reservoir (not shown) and can be configured to supply the catheter 102 with one or more chemicals.

In some embodiments, the system 100 includes a control device 118 along the cable 106. The control device 118 can be configured to initiate, terminate, and/or adjust operation of one or more components of the catheter 102 directly and/or via the console 104. In other embodiments, the control device 118 can be absent or can have another suitable location, such as within the handle 114. The console 104 can be configured to execute an automated control algorithm 120 and/or to receive control instructions from an operator. Furthermore, the console 104 can be configured to provide information to an operator before, during, and/or after a treatment procedure via an evaluation/feedback algorithm 122.

Figure 2A:
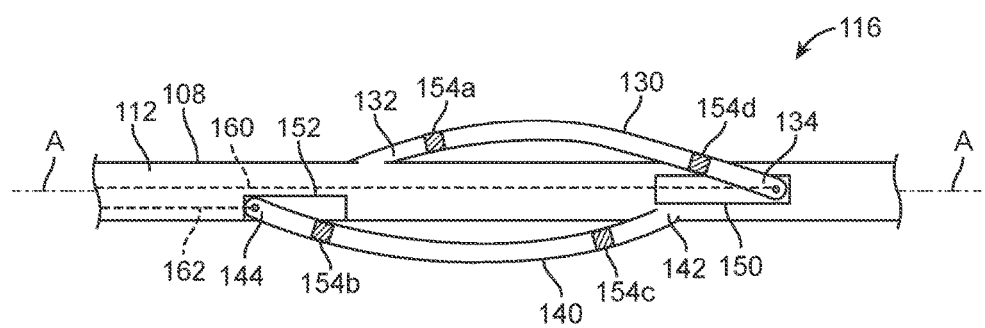
FIGS. 2A-2C are enlarged views of the treatment assembly of FIG. 1.
Figure 2B:
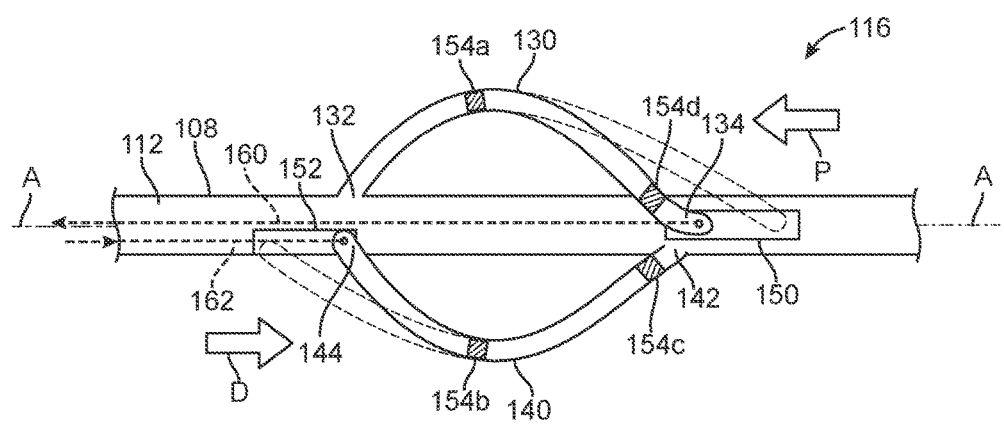
Figure 2C:
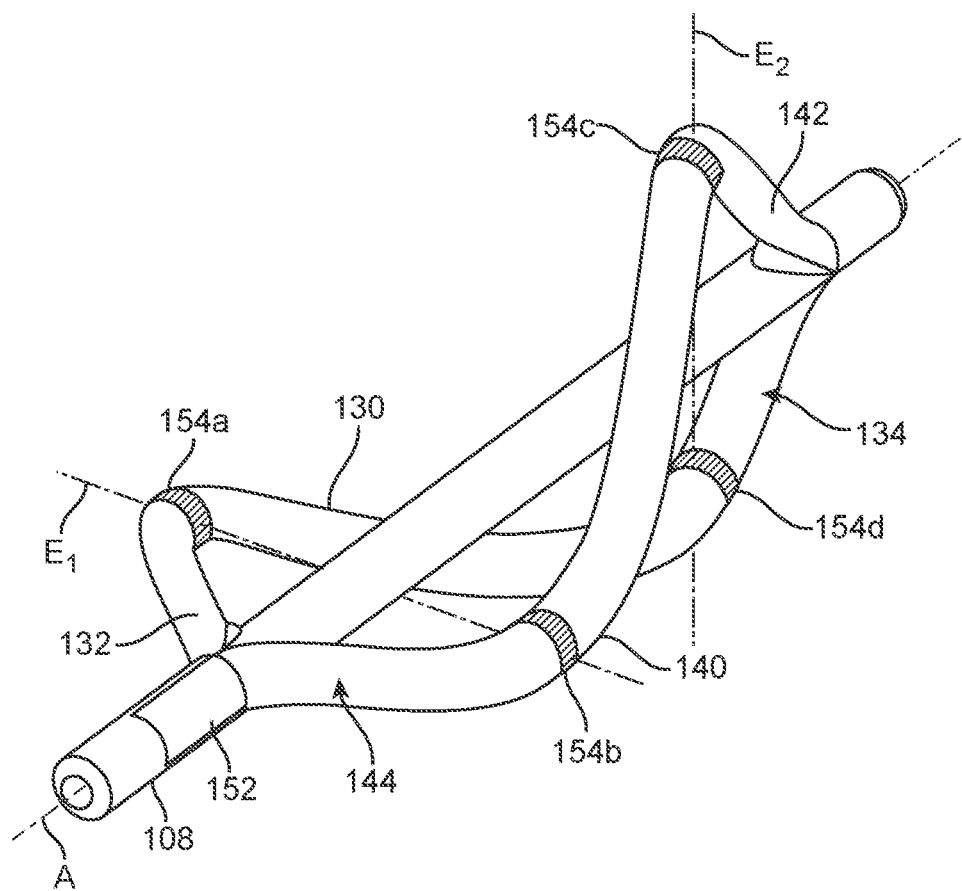

FIGS. 2A-2C are enlarged views of the treatment assembly 116. More specifically, in FIG. 2A, the treatment assembly 116 is shown in a low-profile delivery configuration. In FIGS. 2B and 2C, the treatment assembly 116 is shown in an expanded deployed configuration. Referring first to FIG. 2A, the treatment assembly 116 can include a first strut or expansion member 130 and a second strut or expansion member 140. The first strut 130 is arranged about a longitudinal axis A of the shaft 108 along a first curved path, and the second strut 140 is arranged about the longitudinal axis A along a second curved path offset from the first curved path. The first and second struts 130 and 140 may be composed of metal (e.g., titanium nickel alloy commonly known as nitinol or spring tempered stainless steel). In other embodiments, the first and second struts 130 and 140 may be composed of other suitable materials. Further, in still other embodiments (such as those described below with reference to FIG. 3A-3C), the treatment assembly 116 may include more than two struts or expansion members.

The first and second struts 130 and 140 can be movably (e.g., slidably) connected to the shaft 108. For example, the first strut 130 can include a first fixed end portion 132 coupled to the shaft 108 and a first free end portion 134 slidably engaged with the shaft 108 at a location distal of the first fixed end portion 132. In the illustrated embodiment, the first free end portion 134 is slidably disposed within a first channel or groove 150 of the shaft 108. In other embodiments, however, the first free end portion 134 may be slidably engaged with the shaft 108 via another arrangement. The second strut 140 includes a second fixed end portion 142 coupled to the shaft 108 and a second free end portion 144 slidably engaged with the shaft 108 at a location proximal of the second fixed end portion 142. In the illustrated embodiment, for example, the second free end portion 144 is slidably disposed within a second channel or groove 152. In the present arrangement, the first fixed end portion 132 is adjacent to the second free end portion 144 along the shaft 108, and the first free end portion 134 is adjacent the second fixed end portion 142. In other embodiments, however, the first and second fixed/free ends 132/134/142/144 may have a different arrangement relative to each other along the shaft 108. As described in greater detail below, the first and second struts 130 and 140 are configured to expand radially outward from the shaft 108 in conjunction with the corresponding free end portions 134 and 144 slidably moving in opposite directions along the shaft 108.

The treatment assembly 116 further comprises a plurality of energy delivery elements or electrodes 154 (identified individually as first through fourth electrodes 154a-154d, respectively, and referred to collectively as electrodes 154). Although the electrodes 154 in the illustrated embodiment are shown as ring or band electrodes, it will be appreciated that the electrodes 154 may have various configurations/shapes (e.g., electrodes with generally flat/planar surfaces, electrodes with crescent-shaped cross-sectional profiles, etc.). In the illustrated embodiment, the electrodes 154 are arranged in pairs, including a first pair (comprising the first and second electrodes 154a and 154b) and a second pair (comprising the third and fourth electrodes 154c and 154d). When the treatment assembly 116 is in the low-profile delivery configuration such as shown in FIG. 2A, the electrodes 154 are in a staggered arrangement relative to each other along the longitudinal axis A. As described in greater detail below with reference to FIGS. 2B and 2C, when the treatment assembly 116 is transformed to the expanded deployed configuration, the pairs of electrodes (the first pair 154a/154b and the second pair 154c/154d) are aligned along electrode axes that are orthogonal relative to the longitudinal axis A. In other embodiments, the treatment assembly 116 may have a different number of electrodes 154 and/or the electrodes 154 may have different arrangements/positions relative to each other on the treatment assembly 116. In still further embodiments, the treatment assembly 116 can include energy delivery elements other than electrodes, such as devices suitable for providing other energy-based or chemical-based treatment modalities.

A first control member 160 (shown schematically as a broken line) is operably coupled between the first free end portion 134 of the first strut 130 and the handle 114 (FIG. 1) at the proximal end portion 110 (FIG. 1) of the shaft 108. A second control member 162 (also shown schematically as a broken line) is operably coupled between the second free end portion 144 of the second strut 140 and the handle 114 (FIG. 1). In one embodiment, for example, the first control member 160 comprises a pull wire and the second control member 162 comprises a push wire. In other embodiments, however, the first control member 160 and/or second control member 162 may have a different configuration. The first and second control members 160 and 162 may be manually actuated by one or more operators (not shown) such as levers or knobs to transform the treatment assembly 116 between the delivery configuration (as shown in FIG. 2A) and the deployed configuration.

FIGS. 2B and 2C, for example, are an enlarged side view and an enlarged perspective view, respectively, of the treatment assembly 116 in the deployed configuration. As best seen in FIG. 2B, slidably moving the first free end portion 134 of strut 130 along slot 150 in a proximal direction (as shown by arrow P) via first control member 160 radially expands the first strut 130. Likewise, slidably moving the second free end portion 144 of strut 140 along slot 152 in a distal direction (as shown by arrow D) via second control member 162 radially expands the second strut 140. As mentioned above, for example, in one embodiment the first control member 160 comprises a pull wire adapted to be pushed/pulled by the operator (not shown) to slidably move the first free end portion 134 along slot 150 while the first fixed end portion 132 remains stationary, and the second control member 162 comprises a push wire adapted to be pulled/pushed by the operator to slidably move the second free end portion 144 along slot 152 while the second fixed end portion 142 remains stationary.

As best seen in FIG. 2C, when the treatment assembly 116 is in the deployed configuration, the first pair of electrodes 154a/154b are generally aligned along a first electrode axis $E_1$ orthogonal or transverse to the catheter longitudinal axis A, and the second pair of electrodes 154c/154d are generally aligned along a second electrode axis $E_2$ orthogonal or transverse to the catheter longitudinal axis A. In the illustrated embodiment, the first electrode axis $E_1$ and the second electrode axis $E_2$ are spaced apart from each other along the longitudinal axis A and angularly offset by approximately 90 degrees. In other embodiments, however, the first electrode axis $E_1$ and the second electrode axis $E_2$ may have a different arrangement relative to each other.

Figure 2D:
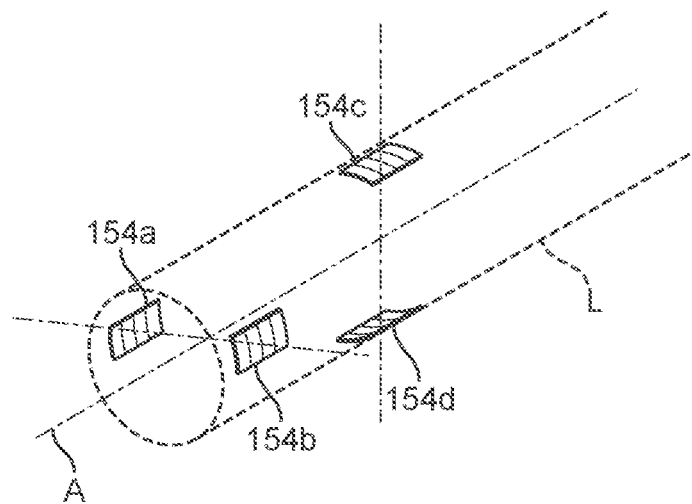
FIGS. 2D and 2E are schematic views of contact regions defined by the treatment assembly of FIG. 1 when the treatment assembly is deployed within a body lumen in accordance with an embodiment of the present technology.
Figure 2E:
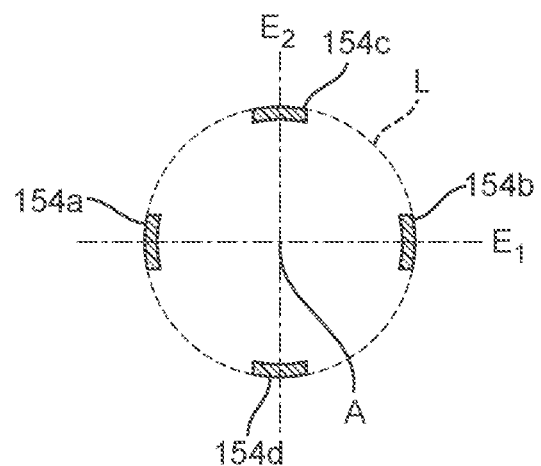

The curved first and second struts 130/140 each have a selected twist/radial sweep such that, when they are in the deployed configuration, the electrodes 154a-d carried by corresponding struts 130/140 are urged into apposition with an inner wall of a body lumen at corresponding contact regions. Referring to FIGS. 2D and 2E, for example, the contact regions of the electrodes 154a-d (shown without the struts 130/140 or shaft 108 for purposes of illustration) can be longitudinally and circumferentially spaced apart along a body lumen L such that the treatment assembly 116 (FIG. 2C) can be used to form a desirable treatment profile.

Figure 3C:
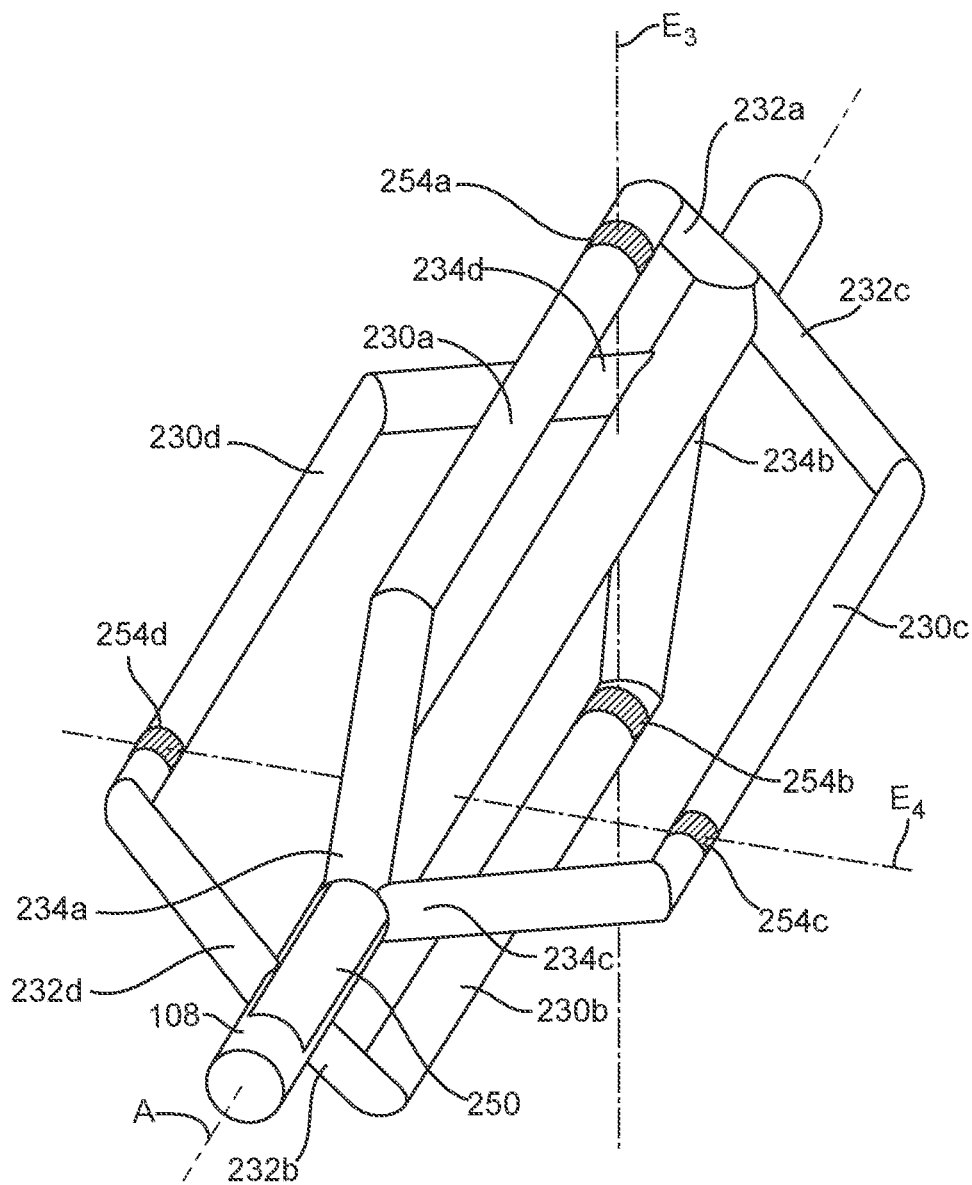

FIGS. 3A-3C are enlarged views of a treatment assembly 216 configured in accordance with another embodiment of the present technology. The treatment assembly 216 may be used with the catheter 102 (FIG. 1), or may be used with other suitable catheters. In FIG. 3A, the treatment assembly is shown in a low-profile delivery configuration. In FIGS. 3B and 3C, the treatment assembly is shown in an expanded deployed configuration. Referring first to FIG. 3A, the treatment assembly 216 differs from the treatment assembly 116 described above in that, rather than having two curved/arched struts 130/140, the treatment assembly 216 includes four struts or members 230 (identified individually as first through fourth struts 230a-230d, respectively, and referred to collectively as struts 230). As described in greater detail below with reference to FIGS. 3B and 3C, the struts 230 are arranged to define a basket-like assembly.

The first strut 230a includes a first fixed end portion 232a coupled to the shaft 108 and a first free end portion 234a slidably engaged with the shaft 108 at a location distal of the first fixed end portion 232a. The second strut 230b includes a second fixed end portion 232b coupled to the shaft 108 and a second free end portion 234b slidably engaged with the shaft 108 at a location proximal of the second fixed end portion 232b. The third strut 230c includes a third fixed end portion 232*c* coupled to the shaft 108 and a third free end portion 234*c* slidably engaged with the shaft 108 at a location distal of the third fixed end portion 232*c*. The fourth strut 230*d* includes a fourth fixed end portion 232*d* coupled to the shaft 108 and a fourth free end portion 234*d* slidably engaged with the shaft 108 at a location proximal of the fourth fixed end portion 232*d*.

The first and third fixed end/free end portions 232*a*/232*c* and 234*a*/234*c*, respectively, may be proximate each other along the shaft 108, and the second and fourth fixed end/free end portions 232*b*/232*d* and 234*b*/234*d*, respectively, may be proximate each other along the shaft 108. In some embodiments, for example, (a) the first and third fixed end/free end portions 232*a*/232*c* and 234*a*/234*c* may be aligned along the longitudinal axis A in both delivery and deployed configurations, and (b) the second and fourth fixed end/free end portions 232*b*/232*d* and 234*b*/234*d* may be aligned along the longitudinal axis A in both delivery and deployed configurations. In other embodiments, however, the free end portions 232*a-d* and/or fixed end portions 234*a-d* of the struts 230 may have a different arrangement relative to each other.

Each strut 230 is configured to carry one or more energy delivery elements or electrodes 254. In the illustrated embodiment, for example, the first through fourth struts 230*a-d* each carry a single electrode 254 (identified individually as first through fourth electrodes 254*a*-254*d*, respectively, and referred to collectively as electrodes 254). In other embodiments, however, the struts 230 may include a different number of electrodes 254 and/or the electrodes 254 may have a different arrangement relative to each other. In still further embodiments, and as noted previously with reference to treatment assembly 116, the treatment assembly 216 may include energy delivery elements other than electrodes, such as devices suitable for providing other energy-based or chemical-based treatment modalities.

FIGS. 3B and 3C are an enlarged side view and an enlarged perspective view, respectively, of the treatment assembly 216 in the expanded deployed configuration. Referring first to FIG. 3B, actuating (e.g., slidably moving) the first and third free end portions 234*a*/234*c* of the first and third struts 230*a*/230*c*, respectively, along slot 250 in a proximal direction (as shown by arrow P) via a first control member 260 transforms the first and third struts 230*a*/230*c* from the constrained, low-profile delivery configuration of FIG. 3A to the expanded, deployed configuration of FIGS. 3B/3C. In one embodiment, for example, the first control member 260 comprises a pull wire operably coupled between (a) the first and third free end portions 234*a*/234*c* and (b) the handle 114 (FIG. 1) at the proximal portion 110 of the shaft 108. The first control member 260 is configured to be pushed/pulled by an operator via manipulation at the handle 114 (FIG. 1) to slidably move the first and third free end portions 234*a*/234*c*. Further details regarding the handle 114 are described below with reference to FIG. 4.

Actuating (e.g., slidably moving) the second and fourth free end portions 234*b*/234*d* of the second and fourth struts 230*b*/230*d*, respectively, along slot 252 in a distal direction (as shown by arrow D) via a second control member 262 transforms the second and fourth struts 230*b*/230*d* from the constrained, low-profile delivery configuration of FIG. 3A to the deployed configuration of FIGS. 3B/3C. In one embodiment, for example, the second control member 262 comprises a push wire operably coupled between (a) the second and fourth free end portions 234*b*/234*d* and (b) the handle 114 (FIG. 1). Like the first control member 260 described above, the second control member 262 is configured to be pushed/pulled by an operator via manipulation at the handle 114 (FIG. 1) to slidably move the second and fourth free end portions 234*b*/234*d*.

As best seen in FIG. 3C and as mentioned previously, the treatment assembly 216 comprises a basket-like assembly in its deployed configuration. Further, in this configuration, a first pair of electrodes (e.g., electrodes 254*a*/254*b*) is generally aligned along a third electrode axis $E_3$ orthogonal or transverse to the catheter longitudinal axis A, and a second pair of electrodes (e.g., electrodes 254*c*/254*d*) is generally aligned along a fourth electrode axis $E_4$ orthogonal or transverse to the longitudinal axis A. In the illustrated embodiment, the third electrode axis $E_3$ is spaced apart from the fourth electrode axis $E_4$ along the longitudinal axis and angularly offset from the fourth electrode axis $E_4$ by approximately 90 degrees. In other embodiments, however, the third electrode axis $E_3$ and the fourth electrode axis $E_4$ may have a different arrangement relative to each other.

Figure 4:
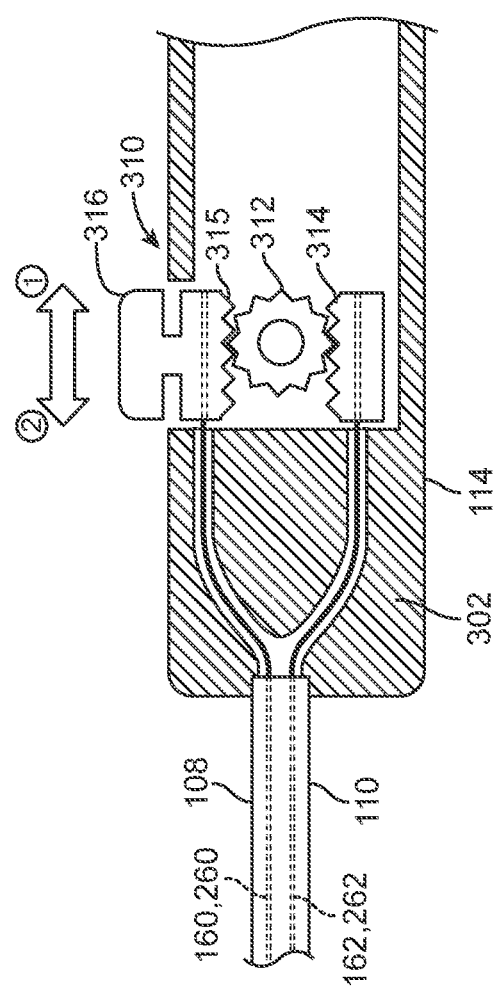
FIG. 4 is a partially schematic side cross-sectional view of a handle assembly configured in accordance with an embodiment of the present technology.

As mentioned above, the treatment assemblies 116/216 may be transformed between the delivery and deployed states via manipulation of the handle 114 by an operator or clinician. FIG. 4, for example, is a partially schematic side cross-sectional view of the handle 114 configured in accordance with an embodiment of the present technology. The illustrated handle 114 may be utilized with the treatment assemblies 116/216 described above with reference to FIGS. 2A-3C, or other suitable treatment assemblies.

The handle 114 comprises a housing 302 and an actuation assembly or mechanism 310 carried by the housing 302. The actuation assembly 310 can include a pinion gear 312 mated with opposing first and second racks 314/315. The first control member 160 (or 260) extends through the shaft 108 and operably couples to first rack 315. The second control member 162 (or 262) extends through the shaft 108 and operably couples to second rack 314. In one embodiment, for example, the first rack 315 is coupled to a button or engagement member 316.

In operation, when an operator pulls the button 316 proximally (as shown by direction 1 of the arrow), the first rack 315 pulls the first control member 160 proximally. Such movement results in simultaneous rotation of the gear 312, thereby moving the second rack 314 in the opposite direction (distally as shown by direction 2 of the arrow). The distal movement of the rack 314 also pushes the second control member 162 in the distal direction. In one embodiment, this sequence deploys the treatment assembly 116 (or 216) from the low-profile delivery configuration to an expanded deployed configuration. Likewise, in this embodiment, when the operator pushes the button 316 distally (in the direction 2 of the arrow), the above-described sequence is reversed to transform the treatment assembly 116 (or 216) from the deployed configuration to the low-profile delivery configuration. In other embodiments, however, the actuation assembly 310 of the handle 114 may have a different arrangement and/or include different features to actuate the treatment assembly 116/216. For example, in some embodiments, the handle 114 may include separate mechanisms to independently actuate the control members 160 and 162 rather than an integrated actuation assembly 310 that simultaneously controls both control members 160 and 162.

Figure 5A:
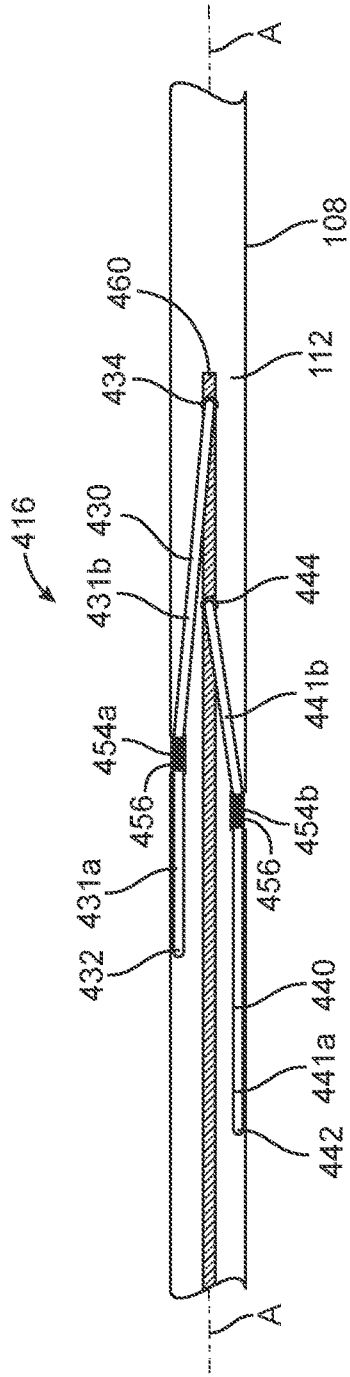
FIGS. 5A and 5B are partially schematic side views of a treatment assembly configured in accordance with yet another embodiment of the present technology.
Figure 5B:
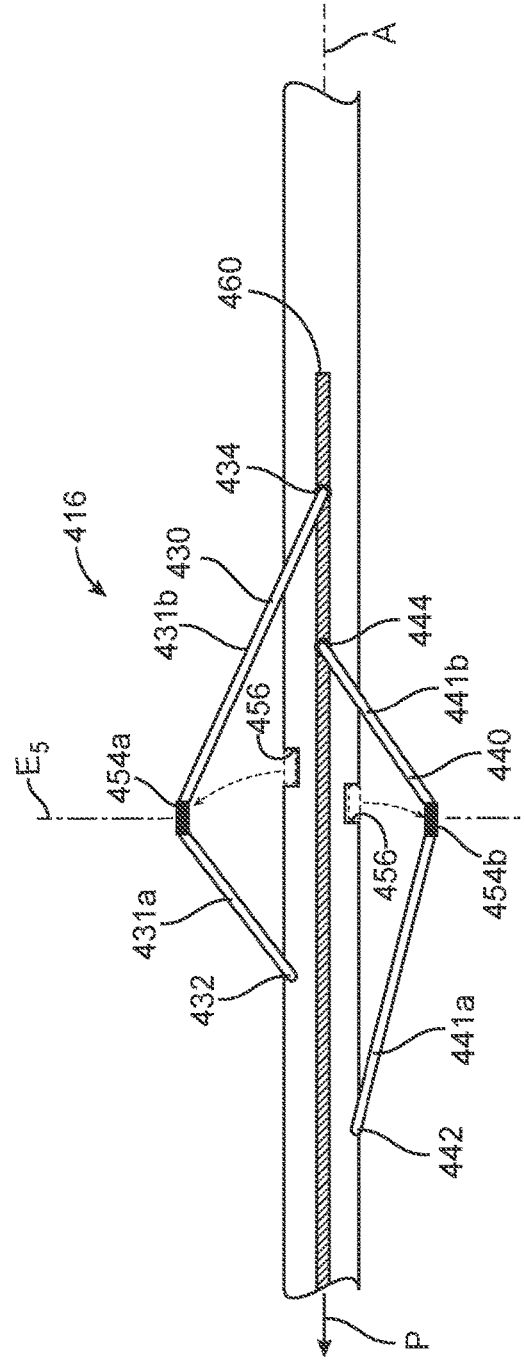

FIGS. 5A and 5B are partially schematic side views of a treatment assembly 416 configured in accordance with yet another embodiment of the present technology. The treatment assembly 416 may be used with the catheter 102 (FIG. 1) or other suitable catheters. In FIG. 5A, the treatment assembly 416 is shown in a low-profile delivery configuration, while in FIG. 5B the treatment assembly is shown in an expanded deployed configuration. Referring to FIGS. 5A and 5B together, the treatment assembly 416 differs from the treatment assemblies 116 and 216 described above in that, rather than having two or more struts that are independently actuated via independent, discrete control members, the treatment assembly 416 includes a single control member 460 (e.g., a pullrod) slidably movable within a lumen of the shaft 108 and connected to two or more strut assemblies of the treatment assembly 416. Actuation of the single control member 460 transforms the multiple strut assemblies of the treatment assembly 416 between delivery and deployed configurations.

In the illustrated embodiment, the treatment assembly 416 includes a first strut assembly 430 and a second strut assembly 440. The first strut assembly 430, for example, includes a first leg 431a, a second leg 431b, and a first energy delivery element or electrode 454a between the first and second legs 431a and 431b. In the illustrated embodiment, the first leg 431a has a first length and the second leg 431b has a second length greater than the first length. The second strut assembly 440 also includes a third leg 441a, a fourth leg 441b, and a second energy delivery element or electrode 454b therebetween. The third and fourth legs 441a/441b of the second strut assembly 440, however have the opposite arrangement from that of the first strut assembly 430. That is, the third leg 441a of the second strut assembly 440 includes a first length and the fourth leg 441b has a second length less than the first length. In other embodiments, however, the first and third legs 431a, 441a and/or the second and fourth legs 431b, 441b may have a different arrangement relative to each other.

The first leg 431a includes a fixed end portion 432 fixedly attached to an outer surface of the shaft 108, e.g by a living hinge. The second leg 431b includes a free end portion 434 coupled to a control member 460 slidably movable within the shaft 108. The third leg 441a of the second strut assembly 440 includes a fixed end portion 442 fixedly attached to the outer surface of the shaft 108 proximal of the fixed end portion 432 of the first leg 431a. The fourth leg 441b includes a free end portion 444 coupled to the control member 460 proximal of the free end portion 434 of the second leg 431b.

As best seen in FIG. 5A of the illustrated embodiment, when the treatment assembly 416 is in the low-profile delivery configuration, the first leg 431a and/or the second leg 431b of the first strut assembly 430 are parallel or generally parallel with the longitudinal axis A. Likewise, the third leg 441a and/or the fourth leg 441b of the second strut assembly 440 are parallel or generally parallel with the longitudinal axis A. In other embodiments, however, the individual legs 431a, 431b, 441a, 441b may have a different arrangement relative the longitudinal axis A and/or each other when the treatment assembly 416 is in the delivery configuration.

In the delivery configuration, the first and second electrodes 454a and 454b are positioned to be received in axially staggered pockets or openings 456 in the shaft 108. This recessed arrangement for the electrodes is expected to further reduce the overall profile of the treatment assembly 416. In other embodiments, however, the shaft 108 may not include openings 456 and the electrodes 454a and 454b may engage an outermost surface of the shaft 108 in the delivery configuration.

Proximal movement of the control member 460 (as shown by the arrow P in FIG. 5B) transforms the first and second strut assemblies 430 and 440 of the treatment assembly 416 from the delivery configuration (FIG. 5A) to the deployed configuration (FIG. 5B). During this transformation, the first and second electrodes 454a and 454b pivot or swing outwardly away from the shaft 108 along separate arcs until the electrodes 454a and 454b are aligned with each other along an electrode axis $E_5$ generally orthogonal or transverse to the catheter longitudinal axis A. As also seen in FIG. 5B, the legs of comparable length (i.e., the first and fourth legs 431a and 441b; the second and third legs 431b and 441a) remain generally parallel to each other during actuation.

In the deployed configuration of FIG. 5B, the first leg 431a and second leg 431b of the first strut assembly 430 together with the longitudinal axis A define a generally triangular deployed shape. Similarly, the third leg 441a and fourth leg 441b of the second strut assembly 440 in conjunction with the longitudinal axis A define a generally triangular deployed shape. In other embodiments, however, the leg geometry can vary. For example, varying the length of one or more of the legs (e.g., the proximal fixed legs—first leg 431a and third leg 441a) can vary the resulting offset distance of the electrodes 454a and 454b from the longitudinal axis A when the treatment assembly 416 is in the deployed configuration. It will also be appreciated that although only two strut assemblies 430 and 440 are shown, the treatment assembly 416 may include additional strut assemblies. As an example, in one embodiment the treatment assembly 416 may include another strut assembly operably coupled to the control member 460 and offset (e.g., 90 degrees) about the shaft 108 from strut assemblies 430 and 440.

Figure 6A:
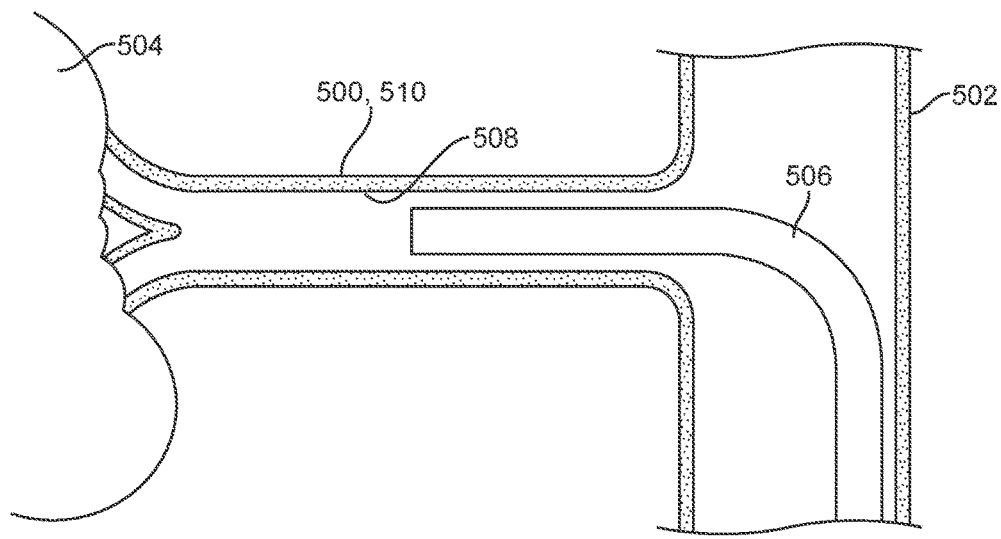
FIGS. 6A-6C are enlarged anatomical side views of the treatment assembly shown in FIG. 1A and associated components located at a treatment location within a renal artery of a human patient.
Figure 6B:
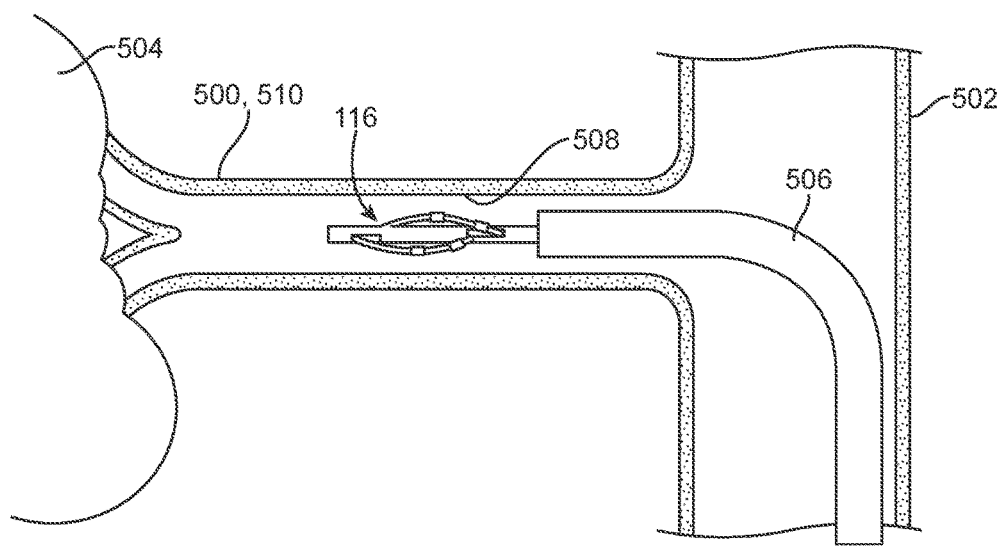
Figure 6C:
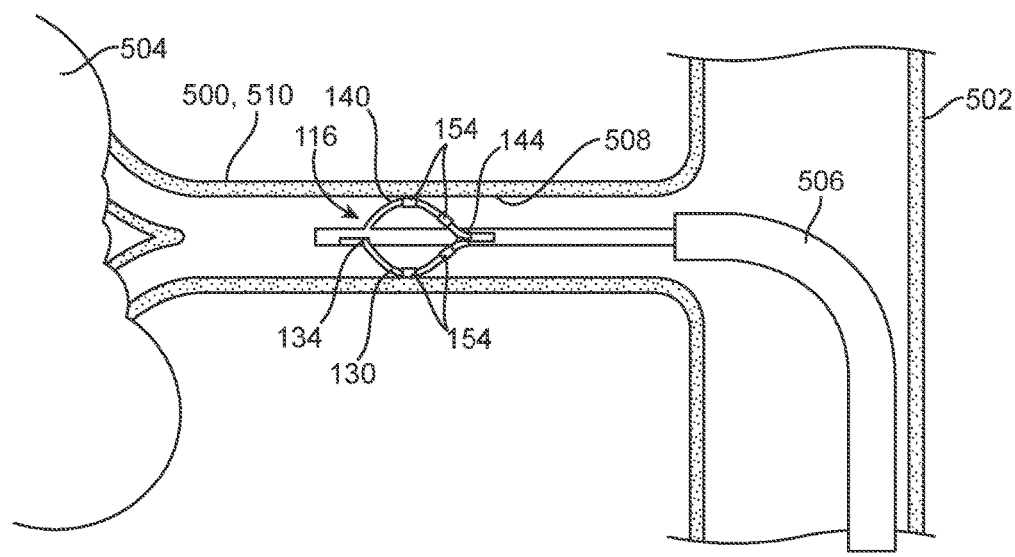

FIGS. 6A-6C are enlarged anatomical side views of the treatment assembly 116 shown in FIG. 1 and associated components being used for renal neuromodulation at a treatment site within a renal artery 500 that extends between an aorta 502 and a kidney 504 in a human patient. The treatment assembly 116 can also be used for other purposes and at treatment locations within other suitable body lumens. To locate the treatment assembly 116 at the treatment location, the catheter 102 can be advanced toward the treatment location while the treatment assembly 116 is radially constrained in a low-profile delivery state within a delivery sheath 506. In FIG. 6A, the treatment assembly 116 is in the delivery state hidden within the delivery sheath 506. It will be understood by persons familiar with the field of catheterization that catheter 102 and sheath 506 would typically be guided, simultaneously or separately, from a vascular puncture site to renal artery 500 using a guiding catheter and/or a medical guidewire, both of which are omitted from FIGS. 6A-6C for simplicity of illustration. In one embodiment, the treatment assembly 116 is configured to fit within a delivery sheath 506 and/or guiding catheter having a 6 F outer diameter.

In FIG. 6B, the treatment assembly 116 is shown in an intermediate state as it transitions from the delivery state to a deployed state. Sheath 506 is shown as having been withdrawn from renal artery 500 sufficiently to expose treatment assembly 116, which remains radially constrained it its delivery configuration. In FIG. 6C, the treatment assembly 116 is shown in the deployed state. As described previously, deploying the treatment assembly 116 can include independently radially expanding struts 130/140 of the treatment assembly 116 by (a) slidably moving the free end portion 134 of strut 130 in one direction (e.g., the proximal direction) via the first control member 160 (FIG. 2B) that extends completely through the shaft 108 from the handle (not shown) to the treatment assembly 116, and (b) slidably moving the free end portion 144 of strut 140 in the opposite direction (e.g., the distal direction) via the second control member 162 (FIG. 2B) that also extends from the handle to the treatment assembly 116. As further noted above, struts 130/140 have a preselected twist/radial sweep such that, when the treatment assembly 116 is in the expanded deployed configuration, electrodes 154 are in apposition with an inner surface 508 of a wall 510 of the renal artery 500. After treatment assembly 116 is deployed at the treatment location, electrodes 154 can be energized to modulate one or more nerves at or near the treatment location.

Renal Neuromodulation

Catheters configured in accordance with at least some embodiments of the present technology can be well suited (e.g., with respect to sizing, flexibility, operational characteristics, and/or other attributes) for performing renal neuromodulation in human patients. Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable treatment locations during a treatment procedure. The treatment location can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery. Various suitable modifications can be made to the catheters described above to accommodate different treatment modalities. For example, the electrodes 154 (FIGS. 2A-2C) can be replaced with transducers to facilitate transducer-based treatment modalities. As another example, the electrodes 154 can be replaced with drug-delivery elements (e.g., needles) to facilitate chemical-based treatment modalities. Other suitable modifications are also possible.

Renal neuromodulation can include an electrode-based or treatment modality alone or in combination with another treatment modality. Electrode-based or transducer-based treatment can include delivering electricity and/or another form of energy to tissue at or near a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at or near a treatment location. For example, neuromodulation in accordance with embodiments of the present technology can include delivering RF energy, pulsed electrical energy, microwave energy, optical energy, focused ultrasound energy (e.g., high-intensity focused ultrasound energy), and/or another suitable type of energy. An electrode or transducer used to deliver this energy can be used alone or with other electrodes or transducers in a multi-electrode or multi-transducer array.

Neuromodulation using focused ultrasound energy (e.g., high-intensity focused ultrasound energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, ultrasound (e.g., intravascular or intraluminal), optical coherence tomography, or another suitable imaging modality). For example, imaging can be used to identify an anatomical position of a treatment location (e.g., as a set of coordinates relative to a reference point). The coordinates can then entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array, which can be curved or straight.

Heating effects of electrode-based or transducer-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of luminal structures that perfuse the target neural fibers. In cases where luminal structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of luminal structures that perfuse the target fibers. In some patients, it can be desirable to heat tissue to temperatures that are sufficient to ablate the target neural fibers or the luminal structures, but that are less than about 90° C. (e.g., less than about 85° C., less than about 80° C., or less than about 75° C.).

Renal neuromodulation can include a chemical-based treatment modality alone or in combination with another treatment modality. Neuromodulation using chemical-based treatment can include delivering one or more chemicals (e.g., drugs or other agents) to tissue at or near a treatment location in a manner that modulates neural function. The chemical, for example, can be selected to affect the treatment location generally or to selectively affect some structures at the treatment location over other structures. The chemical, for example, can be guanethidine, ethanol, phenol, a neurotoxin, or another suitable agent selected to alter, damage, or disrupt nerves. A variety of suitable techniques can be used to deliver chemicals to tissue at or near a treatment location. For example, chemicals can be delivered via one or more needles originating outside the body or within the vasculature or other body lumens. In an intravascular example, a catheter can be used to intravascularly position a treatment assembly including a plurality of needles (e.g., micro-needles) that can be retracted or otherwise blocked prior to deployment. In other embodiments, a chemical can be introduced into tissue at or near a treatment location via simple diffusion through a body lumen wall, electrophoresis, or another suitable mechanism. Similar techniques can be used to introduce chemicals that are not configured to cause neuromodulation, but rather to facilitate neuromodulation via another treatment modality.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments may also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

The methods disclosed herein include and encompass, in addition to methods of practicing the present technology (e.g., methods of making and using the disclosed devices and systems), methods of instructing others to practice the present technology. For example, a method in accordance with a particular embodiment includes intravascularly positioning a catheter at a treatment site within a vessel of a human patient. The intravascular catheter can include an elongated tubular shaft extending along a longitudinal axis, a therapeutic assembly at a distal portion of the shaft, and a pair of electrodes carried by the therapeutic assembly. A control member is operably coupled between the therapeutic assembly and a handle at a proximal portion of the shaft and external to the patient. The method can further include slidably moving the control member in a proximal or distal direction to transform the therapeutic assembly between (a) a low-profile delivery arrangement wherein the pair of electrodes are in a staggered arrangement relative to each other and the longitudinal axis, and (b) a deployed arrangement wherein the pair of electrodes lie in a plane orthogonal to the longitudinal axis.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments of the present technology.

We claim:

1. A catheter apparatus comprising:
   an elongated tubular shaft extending along a longitudinal axis, wherein the elongated shaft includes a proximal portion and a distal portion; and
   a treatment assembly at the distal portion of the shaft and configured to be located at a target location within a blood vessel of a human patient,
   wherein the treatment assembly comprises a basket assembly including (a) a first strut carrying a first electrode, (b) a second strut carrying a second electrode, (c) a third strut carrying a third electrode, and (d) a fourth strut carrying a fourth electrode, and further wherein:
   the first strut includes a first fixed end coupled to the shaft and a first free end slidably engaged with the shaft at a location distal of the first fixed end;
   the second strut includes a second fixed end coupled to the shaft and a second free end slidably engaged with the shaft at a location proximal of the second fixed end;
   the third strut includes a third fixed end coupled to the shaft and a third free end slidably engaged with the shaft at a location distal of the third fixed end; and
   the fourth strut includes a fourth fixed end coupled to the shaft and a fourth free end slidably engaged with the shaft at a location proximal of the fourth fixed end,
   wherein
   when the treatment assembly is in a low-profile delivery configuration, the first, second, third, and fourth electrodes are in a staggered arrangement relative to each other along the longitudinal axis, and
   when the treatment assembly is in a deployed configuration, the first and second electrodes are aligned along a first electrode axis orthogonal relative to the longitudinal axis, and the third and fourth electrodes are aligned along a second electrode axis orthogonal relative to the longitudinal axis, wherein the first and second electrode axes are spaced apart along the longitudinal axis and 90 degrees offset from each other.

2. The catheter apparatus of claim 1 wherein:

the first and third fixed ends are aligned along the longitudinal axis;

the first and third free ends are aligned along the longitudinal axis at a location distal of the first and third fixed ends;

the second and fourth fixed ends are aligned along the longitudinal axis at a location between the first and third fixed ends and the first and third free ends; and the second and fourth free ends are aligned along the longitudinal axis at a location proximal of the first and third fixed ends.

3. The catheter apparatus of claim 1, further comprising:

a first control member operably coupled between (a) the first and third free ends and (b) a handle at the proximal portion of the shaft; and a second control member operably coupled between (c) the second and fourth free ends and (d) the handle, wherein the first and second control members are configured to be actuated in opposite directions to transform the treatment assembly between the low-profile delivery configuration and the deployed configuration.

4. The catheter apparatus of 11 wherein:

the first control member comprises a push wire configured to slidably move the first and third free ends in a distal direction to transform the first and third struts of the treatment assembly between the delivery configuration and the deployed configuration; and the second control member comprises a pull wire configured to slidably move the second and fourth free ends in a proximal direction to transform the second and fourth struts of the treatment assembly between the delivery configuration and the deployed configuration.

5. The catheter apparatus of claim 1 wherein the shaft and the treatment assembly are configured to fit within a guide sheath or guide catheter having a 6 F outer diameter.

6. The catheter apparatus of claim 1 wherein each electrode comprises at least one planar surface.

7. The catheter apparatus of claim 1 wherein each electrode comprises a crescent-shaped cross-sectional profile.

* * * * *